(12) United States Patent
Conn

(10) Patent No.: US 9,297,743 B2
(45) Date of Patent: Mar. 29, 2016

(54) DETERMINATION OF STICK SLIP CONDITIONS

(71) Applicant: Schlumberger Technology Corporation, Sugar Land, TX (US)

(72) Inventor: David Conn, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 380 days.

(21) Appl. No.: 13/721,072

(22) Filed: Dec. 20, 2012

(65) Prior Publication Data

US 2013/0168084 A1    Jul. 4, 2013

Related U.S. Application Data

(60) Provisional application No. 61/580,877, filed on Dec. 28, 2011.

(51) Int. Cl.
| | |
|---|---|
| *E21B 47/06* | (2012.01) |
| *G01N 19/02* | (2006.01) |
| *E21B 44/00* | (2006.01) |
| *E21B 47/09* | (2012.01) |

(52) U.S. Cl.
CPC ............... *G01N 19/02* (2013.01); *E21B 44/00* (2013.01); *E21B 47/06* (2013.01); *E21B 47/091* (2013.01)

(58) Field of Classification Search
CPC .................................. E21B 44/00; E21B 47/06
See application file for complete search history.

(56) References Cited

U.S. PATENT DOCUMENTS

| | | | |
|---|---|---|---|
| 5,117,926 A | 6/1992 | Worrall et al. | |
| 5,721,376 A * | 2/1998 | Pavone et al. | ............... 73/152.47 |
| 6,174,001 B1 | 1/2001 | Enderle | |
| 6,892,812 B2 | 5/2005 | Niedermayr et al. | |
| 7,082,821 B2 | 8/2006 | Chen et al. | |
| 2004/0206170 A1 | 10/2004 | Chen et al. | |
| 2011/0232966 A1 | 9/2011 | Kyllingstad | |

OTHER PUBLICATIONS

A. Kyllingstad, G.W. Halsey, "A Study of Slip Stick Motion of the Bit," SPE Drilling Engineering, Dec. 1988, pp. 369-373.
Lasseter, T., Karakas, M., and Schweltzer, J., "Interpreting an RFT-Measured Pulse Test with a Three-Dimensional Simulator" by SPE 14878, Mar. 1988.
Bunn, G.F., and Yaxley, L.M., "Design, Implementation, and Interpretation of a Three-Dimensional Well Test in the Cormorant Field, North Sea," SPE 15858, Oct. 1986.
Saeedi, J., and Standen, E., "Layer Pulse Testing Using a Wireline Formation Tester" SPE 16803, Sep. 1987.

(Continued)

*Primary Examiner* — William P Neuder

(57) ABSTRACT

A method for determining stick slip conditions. The method may include disposing an operating apparatus in fluid communication with a pressure wave transmission medium. At least one pressure measurement device may be disposed at least partially within the pressure wave transmission medium and at some distance from the operating apparatus. One or more pressure waves generated by the operating apparatus may be measured within the pressure wave transmission medium with the at least one pressure measurement device and pressure measurement data may be generated therefrom. The pressure measurement data from the at least one pressure measurement device may be transmitted to a data acquisition system. The pressure measurement data may be analyzed to detect one or more stick slip conditions from one or more variations in the pressure measurement data.

22 Claims, 6 Drawing Sheets

(56) References Cited

OTHER PUBLICATIONS

Bunn, G.F., Wittman, M.J., Morgan, W.D., and Curnutt, R.C., "Distributed Pressure Measurements Allow Early Quantification of Reservoir Dynamics in the Jene Field" SPE 17682, Mar. 1991.

Yaxley, L.M., and Blaymires, J. M "A Field Example of Interference Testing Across a Partially Communicating Fault," SPE 19306, 1989.

Kaneda, R., Saeedi, J., and Ayestaran, L.C., "Interpretation of a Pulse Test in a Layered Reservoir," SPE 21337, Dec. 1991.

Halsey, G.W., Kyllingstad, A., Kylling, A., "Torque Feedback Used to Cure Slip-Stick Motion," Paper SPE. 18049 presented at SPE Annual Technical Conference and Exhibition, Houson, TX, Oct. 5-8, 1988.

Kyllingstad et al., "A New Stick-Slip Prevention System", SPE/IADC 119660 presented at the SPE/IADC Drilling Conference and Exhibition, Amsterdam, The Netherlands, Mar. 17-19, 2009.

* cited by examiner

DETERMINATION OF STICK SLIP CONDITIONS

RELATED APPLICATIONS

This application claims the benefit of a related U.S. Provisional Application Ser. No. 61/580,877 filed 28 Dec. 2011, entitled "Determination of Stick Slip Conditions," to David K. Conn, the disclosure of which is incorporated by reference herein in its entirety.

BACKGROUND

A stick slip condition or phenomenon is the spontaneous jerking motion that occurs while two objects are sliding over each other. Stick slip is caused by the surfaces alternating between sticking to each other and sliding over each other, with a corresponding change in the friction coefficient between them. The static friction coefficient between two surfaces can be larger than the kinetic friction coefficient. If an applied force is large enough to overcome the static friction, then the reduction of the friction to the kinetic friction can cause a sudden jump in the velocity.

Stick slip can occur during drilling operations and adversely affects the overall drilling performance by causing the premature failure of drilling components. Drillers desire to predict and/or reduce stick slip conditions to enhance drilling activities. The physics behind the actual phenomenon can be complicated due to differing borehole geometries, differing geological conditions and equipment used.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A method for determining stick slip conditions is disclosed. The method includes disposing an operating apparatus in fluid communication with a pressure wave transmission medium. Disposing at least one pressure measurement device at least partially within the pressure wave transmission medium and at some distance from the operating apparatus. Measuring one or more pressure waves generated by the operating apparatus within the pressure wave transmission medium with the at least one pressure measurement device and generating pressure measurement data therefrom. Transmitting the pressure measurement data from the at least one pressure measurement device to a data acquisition system. Analyzing the pressure measurement data to detect one or more stick slip conditions from one or more variations in the pressure measurement data.

A method for determining stick slip conditions on a drill string in a borehole. The method includes disposing at least one pressure measurement device in fluid communication with a drilling fluid disposed within a borehole. Disposing a bottom hole assembly coupled to a drill string within the borehole and in fluid communication with the drilling fluid. Measuring pressure waves within the drilling fluid and transmitting pressure measurement data to a data acquisition system. Detecting a stick slip condition from one or more variations in the pressure measurement data. Comparing the one or more variations in the pressure measurement data to a threshold. Controlling a progression of the drill string within the borehole if the one or more variations in the pressure measurement data exceed the threshold.

A system for detecting stick slip conditions is disclosed. The system includes a drill string disposed in a borehole at a well site. A first at least one pressure measurement device disposed at some distance from the drill string, wherein the first at least one pressure measurement device is in fluid communication with a drilling fluid disposed within the borehole, and wherein the first at least one pressure measurement device is adapted to measure one or more pressure waves within the drilling fluid. A first data acquisition system disposed at a surface location of the well site, wherein the first data acquisition system is adapted to receive and process pressure measurement data from the first at least one pressure measurement device, and wherein the first data acquisition system is adapted to detect one or more stick slip conditions from one or more variations in the pressure measurement data and adapted to compare the one or more variations in the pressure measurement data to a threshold.

FIGURES

So that the recited features may be understood in detail, a more particular description, briefly summarized above, may be had by reference to one or more embodiments, some of which are illustrated in the appended drawings. It is to be noted, however, that the appended drawings are illustrative embodiments, and are, therefore, not to be considered limiting of its scope.

DETAILED DESCRIPTION

Figure 1:
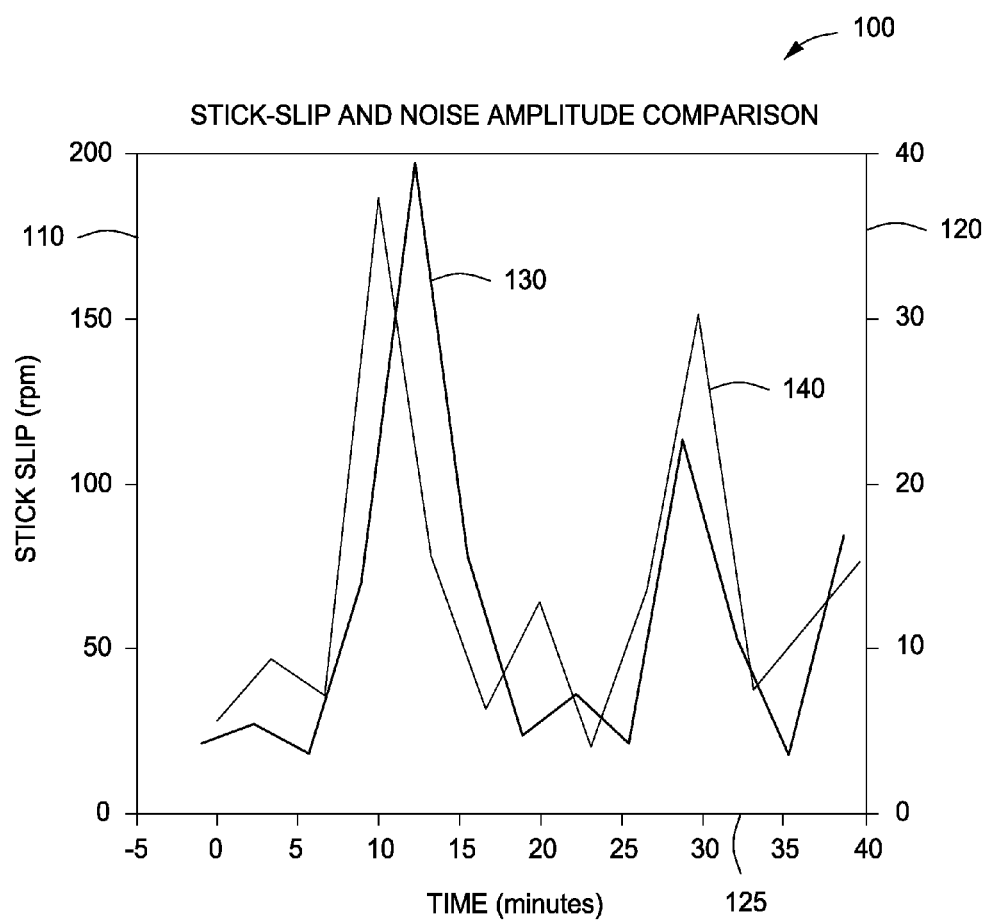
FIG. 1 depicts a chart that plots measured stick slip data and drilling noise amplitude data both as a function of time, according to one or more embodiments disclosed.

FIG. 1 depicts a chart 100 that plots measured stick slip data 110 and drilling noise amplitude data 120 both as a function of time 125, according to one or more embodiments. The plot was generated from data taken from drilling activities where poor telemetry signal data acquisition was experienced. The poor telemetry acquisition was due to one or more noise signals found within the telemetry signal data. The observed one or more noise signals appeared within frequency bands or noise frequency bands around about 0.3 Hz to about 0.6 Hz. The noise frequency bands can be at frequencies ranging from about 0.01 Hz to about 1 Hz or more. In order to determine the cause of the one or more noise signals, pressure traces, bottom hole assembly (BHA) data, formation data, mud reports, and other information were gathered from several drilling jobs. This data was then correlated with the locations and strength of the one or more noise signals. A strong correlation was observed between the measured stick slip data, as represented by line 130, and noise amplitude data from the one or more noise signals as represented by line 140. It has been discovered from these and other observations that the one or more noise signals can come from one or more pressure waves generated from one or more stick slip conditions and these one or more pressure waves can be measured and correlated to the one or more stick slip conditions. The one or more pressure waves can be correlated to the one or more stick slip conditions by searching for variations or distinguishable peaks in the one or more pressure waves consistent with stick slip conditions. The pressure wave measurements can be converted into pressure measurement data. Spectral analysis can be performed on the pressure measurement data, and an analysis of the frequency spectrum of the pressure measurement data can be performed to detect the one or more stick slip conditions from one or more variations in the pressure measurement data.

Spectral analysis techniques can be used to analyze the telemetry signal data. Spectral analysis can be performed on any of the data based on time domain measurements of the one or more noise signals, using an analogue or digital spectral analyzer, implemented in hardware and/or software. Spectral analysis approaches can be parametric and/or nonparametric. They can include, but are not limited to, Fourier Transforms, Discrete-time Fourier Transforms, Fast Fourier Transforms (FFT), inverse Fourier Transforms, the Burg method, Autoregressive model-based methods, Welch's methods, Thompson's Multitaper methods, and/or eigenanalysis-based methods such as Multiple Signal Classification.

The telemetry signal data can be searched to determine one or more noise frequency bands from the one or more noise signals. At least one noise frequency band can be searched to detect the one or more stick slip conditions from one or more variations in the telemetry signal data. A comparison can be performed between the one or more variations in the telemetry signal data and the one or more variations in the pressure measurement data. The comparison can be performed to confirm that at least one stick slip condition exists.

Figure 2:
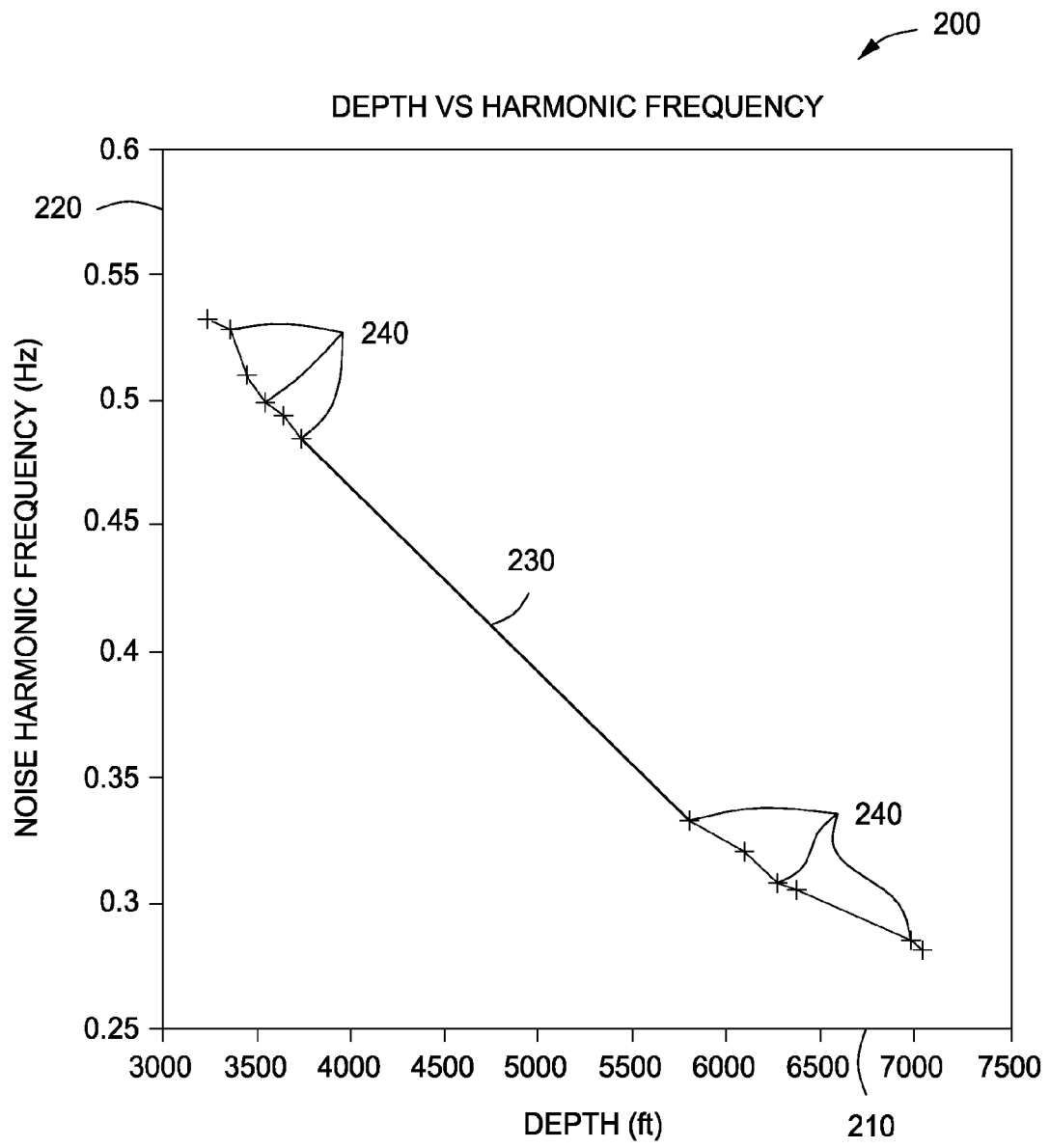
FIG. 2 depicts a chart that plots noise harmonic frequency data taken during drilling versus the depth of a drill string used for drilling, according to one or more embodiments disclosed.

FIG. 2 depicts a chart 200 that plots noise harmonic frequency data 220 taken during drilling versus the depth 210 of a drill string used for drilling, according to one or more embodiments. Here, as the depth 210 increases, the noise harmonic frequency 240 at various depths decreases. It has been discovered that the measured noise harmonic frequency 240 at a given depth can be correlated to the resonance frequency of the drill string with a length that corresponds to the given depth. The resonance frequencies for the drill string are plotted along curve 230. The noise harmonic frequency 240 can be at frequencies ranging from about 0.01 Hz to about 1 Hz or more.

It has been discovered that the resonance frequencies of the drill string can be used to indicate stick slip conditions within the pressure measurement data and/or the telemetry signal data from the drill string taken during stick slip conditions. For example, spectral analysis techniques can be used to analyze the pressure measurement data and/or the telemetry signal data from the drill string. Knowing the length of the drill string, the resonance frequencies of the drill string can be estimated, and the pressure measurement data and/or the telemetry signal data can be searched within the estimated resonance frequencies and/or within the noise spectrums for variations in the pressure measurement data and/or the telemetry signal data. The one or more variations in the pressure measurement data and/or the telemetry signal data can indicate stick slip conditions.

According to the work of Kyllingstad and Halsey, the drill string can be modeled as a pendulum, with the drill pipe as the string and a BHA as the weight. In this case, the resonant frequency can be given by $$\omega^2 = \frac{S}{J} \qquad \text{(Eq. 1)}$$

Where, S is torsional stiffness, given by $$S = \frac{GI_1}{L_1};$$

J is the effective moment of inertia, which can be approximated as $$J = \rho I_1 \frac{L_1}{3} + \rho I_2 L_2;$$

G is the shear modulus of the drill string; $I_1$ is the polar moment of inertia of the drill pipe; $I_2$ is the polar moment of inertia of the BHA; $L_1$ is the length of drill pipe; $L_2$ is the length of the BHA; $\rho$ is the density of the drill string. For additional details, see the following references: "A New Stick-Slip Prevention System" by Kyllingstad, A.; SPE; and Nessjoen, P.; SPE/IADC 119660, March 2009; and "A Study of Slip/Stick Motion of the Bit" by Kyllingstad, A; and Halsey, G; SPE Drilling Engineering, December 1988, pp 370-373.

Figure 3:
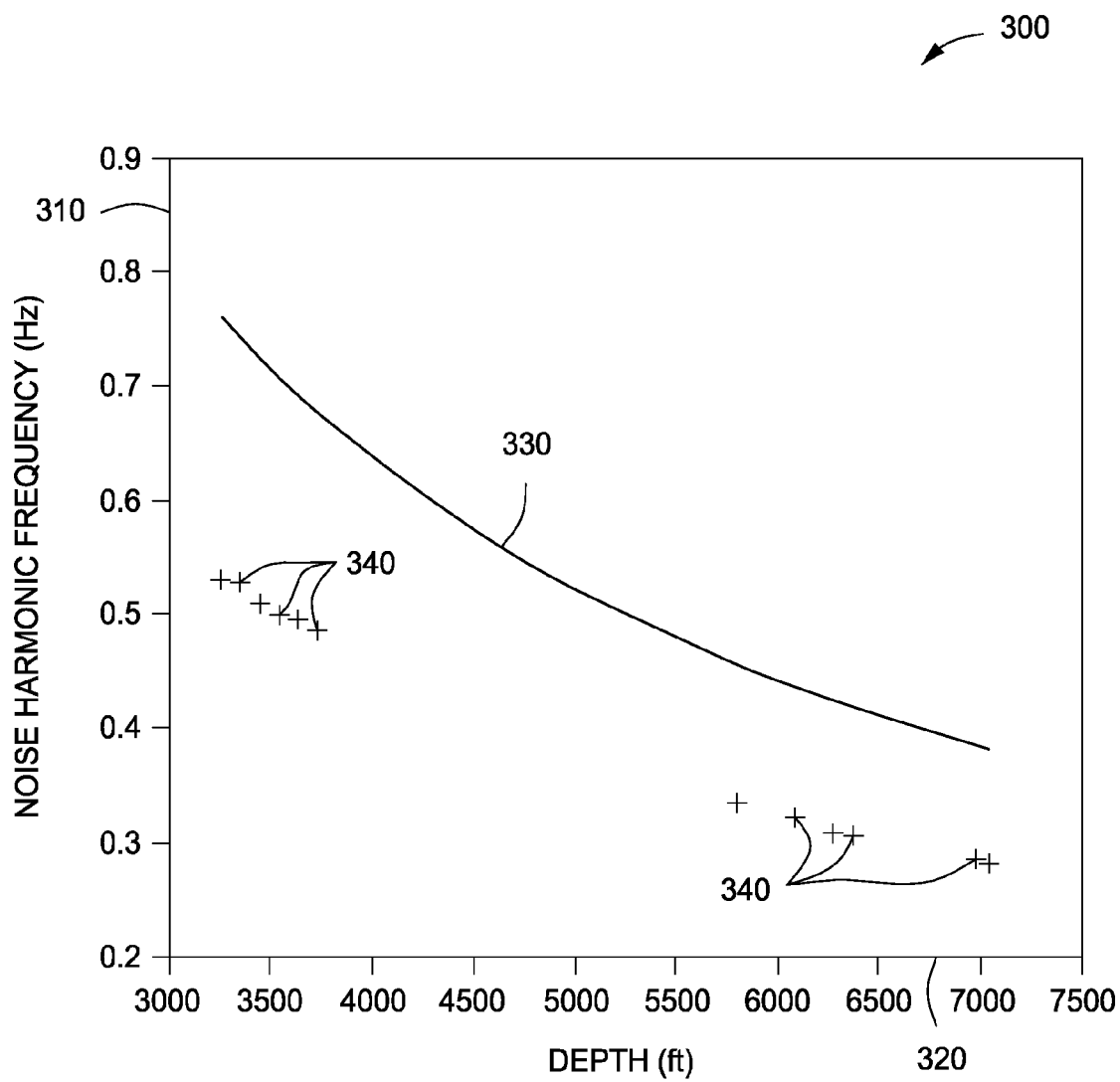
FIG. 3 depicts a chart that plots noise harmonic frequencies from measured noise harmonic frequency data versus depth as compared to the output from a closed end model of drill string resonance frequencies versus depth, according to one or more embodiments disclosed.

FIG. 3 depicts a chart 300 that plots noise harmonic frequencies 310 from measured noise harmonic frequency data 340 versus depth 320 as compared to the output from a closed end model 330 of drill string resonance frequencies versus depth 320, according to one or more embodiments. The closed end curve 330 was generated using Eq. 1 from data from a specific drilling job that corresponds to some of the field data shown in FIG. 1 and FIG. 2 above where, $L_2$ is 307.57 m $$I_2 = \frac{(6.75^4 - 2.8125^4)\pi}{32} * inchss^t tometsrs^t = 1.64s^{-t}m^t$$

$$I_1 = \frac{(5^4 - 4^4)\pi}{32} * inches^4 tometers^4 = 1.51s^{-5}m^4$$

$$G = 81.4e^9 Pa$$

$\rho$ is 7,890 kg/m$^3$

The noise harmonic frequency data 340 was taken from the same field data. The results for various depths from the drilling job are given in FIG. 3. The difference between the plot of the noise harmonic frequency data 340 and the curve 330 can be attributed to the time travel of torsional waves.

Figure 4:
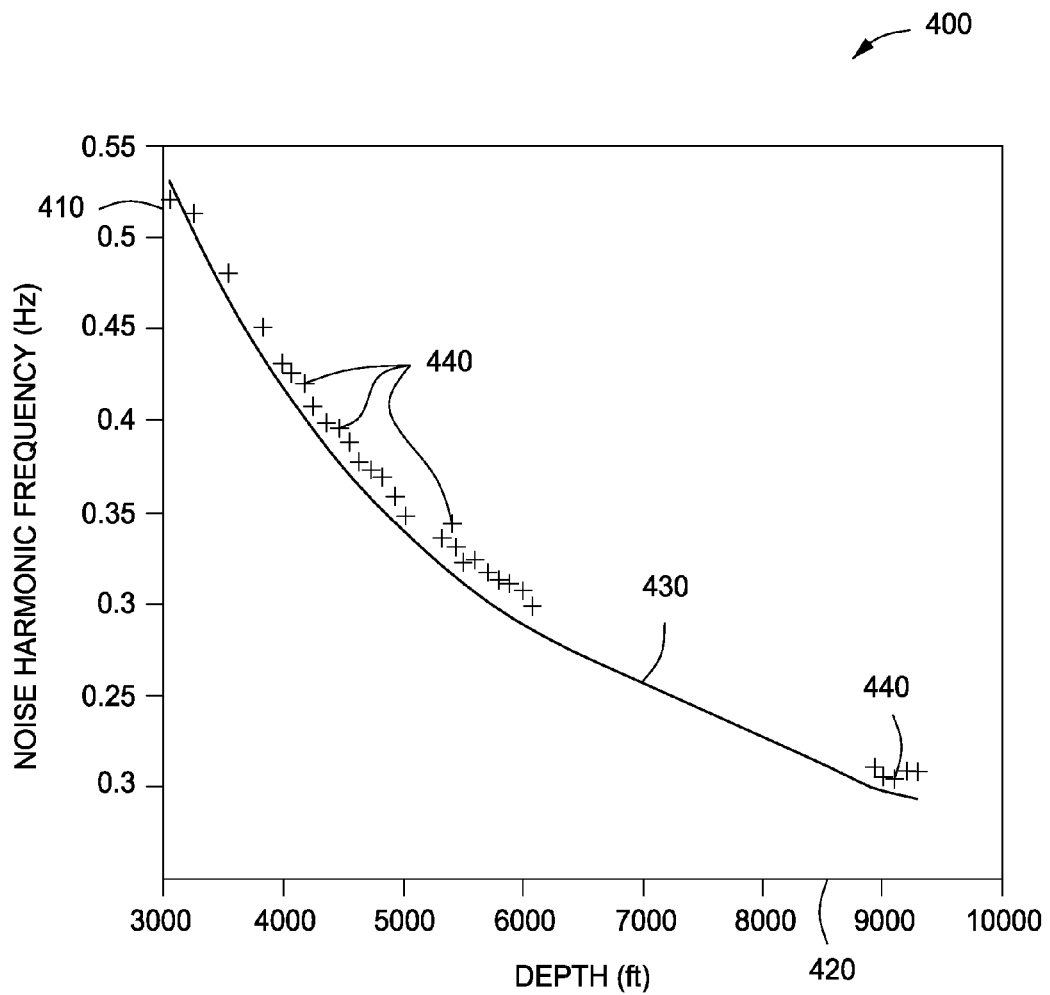
FIG. 4 depicts a chart that plots noise harmonic frequencies from measured noise harmonic frequency data versus depth as compared to the output from a resonance frequency curve that accounts for the time travel of torsional waves, according to one or more embodiments disclosed.

FIG. 4 depicts a chart 400 that plots noise harmonic frequencies 410 from measured noise harmonic frequency data 440 versus depth 420 as compared to the output from a resonance frequency curve 430 that accounts for the time travel of torsional waves, according to one or more embodiments. To account for the travel time of torsional waves, a model described by Kyllingstad and Nessjoen can be used. The model can be expressed as:

$$\omega_s = \frac{\left(\pi - 2\tan^{-1}\left(\frac{\omega_s J}{\zeta}\right)\right)c}{2L} \quad \text{(Eq. 2)}$$

Where c is the shear wave velocity, $$\sqrt{\frac{G}{p}};$$

and $\zeta$ is given by $I\sqrt{pG}$.

Eq. 1 and/or Eq. 2 can be used to estimate and/or calculate the resonance frequencies of a drill string, and these estimates and/or calculations can be used to search for slick slip indicators within the telemetry signal data from drilling operations.

Figure 5:
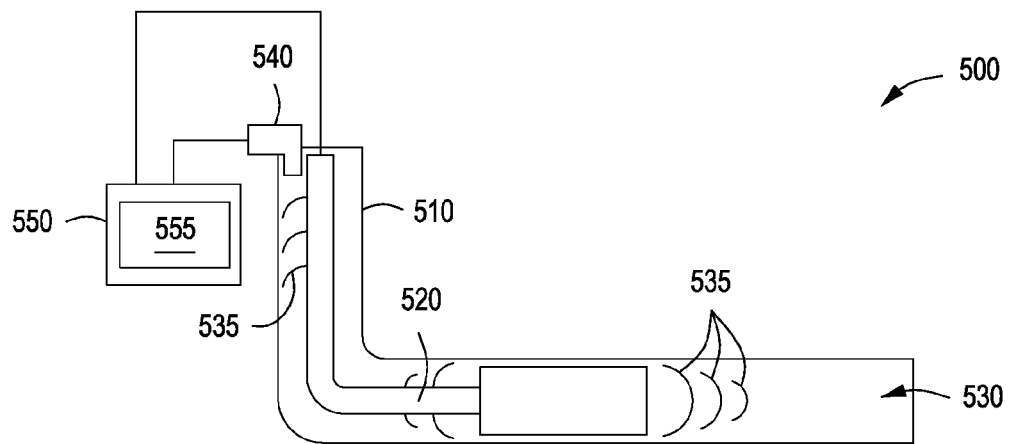
FIG. 5 depicts an illustrative system in which embodiments of Determination of Stick Slip Conditions can be implemented, according to one or more embodiments disclosed.

FIG. 5 illustrates an example system 500 in which embodiments of Determination of Stick Slip Conditions can be implemented, according to one or more embodiments. From the observations above and other observations, it has been discovered that the one or more stick slip conditions can be measured anywhere within a pressure wave transmission medium in communication with an apparatus undergoing stick slip conditions. For example, an apparatus 520 can be disposed within and can be operating within a trough 510 and the apparatus 520 can undergo one or more stick slip conditions while disposed within the trough 510. The trough 510 can be at least partially filled with a fluid or pressure wave transmission medium 530 capable of transmitting one or more pressure waves 535, and the apparatus 520 can be in fluid communication with and can be generating the one or more pressure waves 535 within the fluid 530. The fluid 530 can be any liquid including, but not limited to, water, drilling fluid, drilling mud, or any fluid or combination of fluids known that can transmit the one or more pressure waves 535 through the trough 510. At least one pressure measurement device 540 can be disposed at least partially within the fluid 530 and can detect and/or measure the one or more pressure waves 535. The at least one pressure measurement device 540 can be disposed anywhere within the fluid 530. The at least one pressure measurement device 540 can be disposed at some distance from the apparatus 520. The at least one pressure measurement device 540 can be disposed anywhere on or within the apparatus 520.

A data acquisition system 550 can include a computer 555 and can collect pressure measurement data generated by the at least one pressure measurement device 540 from the measurement of the one or more pressure waves 535. There can be one or more data acquisition systems 550. The one or more computers 555 can also collect telemetry signal data generated from the apparatus 520, and/or can collect telemetry signal data from other devices, not shown. The one or more computers 555 can search the pressure measurement data from the at least one pressure measurement device 540, the telemetry signal data from the apparatus 520, and/or the telemetry signal data from the other devices to identify the one or more variations in the pressure measurement data and/or the telemetry signal data and detect the one or more stick slip conditions from the one or more variations in the pressure measurement data and/or the telemetry signal data. The one or more variations in the pressure measurement data and/or the telemetry signal data can occur around the resonance frequency of the apparatus 520 and can be prominent as compared to other data within the pressure measurement data and/or the telemetry signal data. Although the data acquisition system 550 is illustrated with the one or more computers 555 disposed therein, the data acquisition system 550 can be fully or partially integrated with the one or more computers 555, and no limitations should be assumed from the illustration.

The telemetry signal data from the apparatus 520 can be interfered with by the one or more pressure waves 535, and the interference can be seen within the telemetry signal data from the apparatus 520 as noise. The pressure measurement data from the at least one pressure measurement device 540 can be interfered with by operations associated with the apparatus 520. The one or more computers 555 can use numerical analysis techniques to identify data within the telemetry signal data and/or the pressure measurement data that is the result of the operations associated with the apparatus 520 and can distinguish the data that is associated with the operations associated with the apparatus 520 from the variations in the data that indicates the one or more stick slip conditions.

The noise can be within frequency bands that can be detected using spectral analysis techniques. The spectral analysis techniques can be performed by the one or more computers 555 to identify variations in the telemetry signal data from the apparatus 520 and/or to identify variations in the pressure measurement data from the at least one pressure measurement device 540. The variations in the telemetry signal data and/or the pressure measurement data can be used to detect the one or more stick slip conditions. The variations in the telemetry signal data and the pressure measurement data can be compared to confirm that at least one stick slip condition exists.

The apparatus 520 can have one or more known, estimated, and/or calculable resonance frequencies. The one or more computers 555 can electronically search the telemetry signal data from the apparatus 520 and/or the pressure measurement data from the at least one pressure measurement device 540, using at least one known spectral analysis technique, within frequency bands in the ranges of at least one known, estimated, and/or calculable resonance frequency of the apparatus 520 to detect the one or more stick slip conditions from the variations in the data within the resonance frequency bands.

The variations in the telemetry signal data can be compared to the pressure measurement data and utilized as a further indication of the one or more stick slip conditions. The variations in the telemetry signal data and/or pressure measurement data can be compared to at least one threshold. The variations in the telemetry signal data and/or pressure measurement data can be analyzed by the one or more computers 555 and compared to at least one threshold. The threshold can be a preset threshold. If the comparison indicates that the variations meet and/or exceed the at least one threshold, at least one operational parameter of the apparatus can be changed such that the one or more stick slip conditions can be at least moderated. For example, the at least one operational parameter can be slowed or accelerated.

Figure 6:
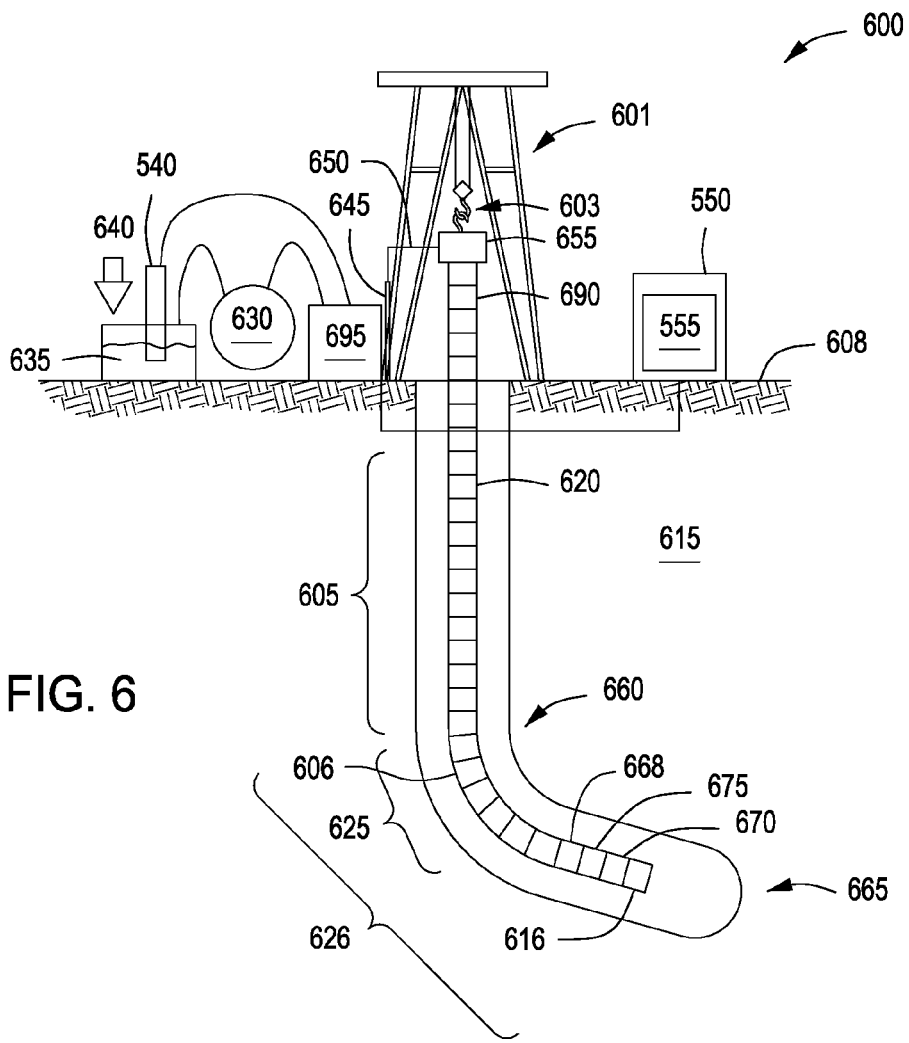
FIG. 6 illustrates an example well site in which embodiments of Determination of Stick Slip Conditions can be implemented, according to one or more embodiments disclosed.

FIG. 6 illustrates an example well site 600 in which embodiments of Determination of Stick Slip Conditions can be implemented, according to one or more embodiments. In accordance with the present disclosure, a well site 600 can include a wellbore or borehole 665 and apparatus. The apparatus at the well site 600 can be altered, as necessary, due to field considerations encountered. The well site 600 can include a drill string 605 having one or more segments that can extend from a drill rig 601 into a borehole 665 in a zone of the formation of reservoir 615. The drill string 605 can employ a telemetry system 606 for transmitting data from downhole to the surface. The at least one pressure measurement device 540 can be in fluid communication with a drilling fluid 635. The at least one pressure measurement device 540 can be disposed anywhere within the borehole 665 at some distance from the drill string 605 and/or the BHA 626. The at least one pressure measurement device 540 can be disposed anywhere along the exterior or within the drill string 605 and/or the BHA 626. The at least one pressure measurement device 540 can be disposed on the surface 608 of the well site 600 in fluid communication with the drilling fluid 635. The at least one pressure measurement device 540 can be disposed on the surface 608 of the well site 600 in fluid communication with the drilling fluid 635 and at least a second pressure measurement device 540 can be disposed anywhere along the exterior or within the drill string 605 and/or the BHA 626.

The drill string 605 can use any type of telemetry system or any combination of telemetry systems, such as mud pulse telemetry, electromagnetic, acoustic and/or wired drill pipe. The BHA 626 can be suspended at the end of the drill string 605. In an embodiment, the BHA 626 can include a plurality of measurement while drilling ("MWD") or logging while drilling ("LWD") tools 625. For example, one or more of the measurement while drilling or logging while drilling tools 625 can include a formation pressure while drilling tool.

Logging while drilling tools 625 can be disposed within the BHA 626 and can include a thick walled housing, commonly referred to as a drill collar, and can include one or more of a number of logging devices. The logging while drilling tool can measure, process, and/or store information therein, as well as communicate with equipment disposed at the surface of the well site 600.

Measurement while drilling tools 625 can include one or more of the following measuring devices: a modulator, a weight on a drill bit measuring device, a torque measuring device, a vibration measuring device, a shock measuring device, a direction measuring device, an inclination measuring device, and/or any other device.

Measurements taken by the BHA 626 or other tools and sensors dispose on or within the drill string 605 can be transmitted to the data acquisition system 550 for analysis. The data acquisition system 550 can include the one or more computers 555.

Figure 7:
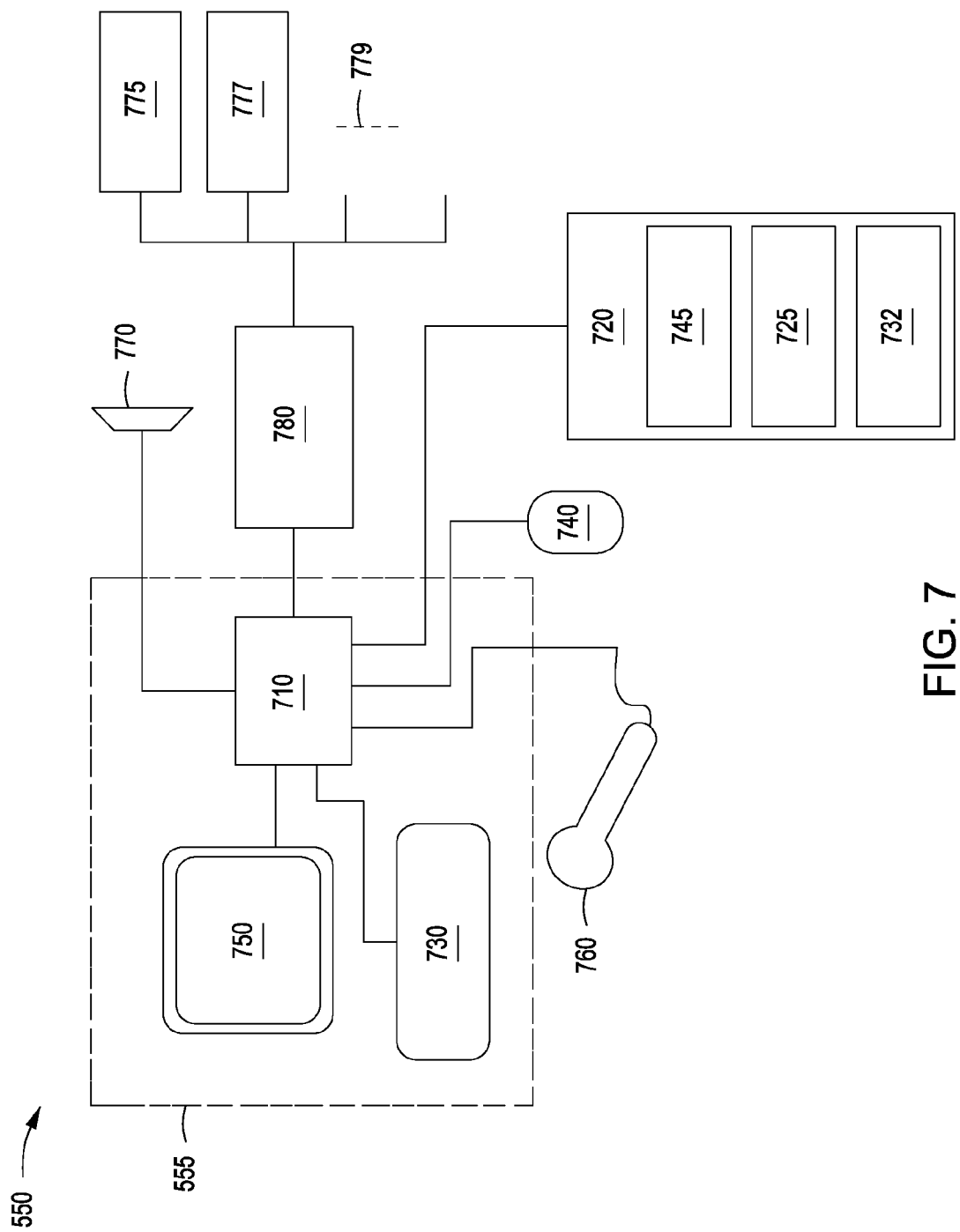
FIG. 7 illustrates the data acquisition system on which embodiments of Determination of Stick Slip Conditions can be implemented, according to one or more embodiments disclosed.

FIG. 7 illustrates the data acquisition system 550 on which embodiments of Determination of Stick Slip Conditions can be implemented, according to one or more embodiments. The data acquisition system 550 can include one or more computers 555 that each can include one or more central processing units 710, one or more input devices or keyboards 730, and one or more monitors 750 on which one or more software applications can be executed. The one or more computers 555 can each also include one or more memories 720 as well as additional input and output devices, such as a mouse 740, one or more microphones 760, and one or more speakers 770. The mouse 740, the one or more microphones 760, and the one or more speakers 770 can be used for, among other purposes, universal access and voice recognition or commanding. The one o more monitors 750 can be touch-sensitive to operate as an input device as well as a display device.

The one or more computers 555 can interface with a database 777; a support computer or processor 775; pressure measurement data, BHA telemetry signal data, other telemetry signal data, other databases, and/or other processors 779; and/or the Internet via the interface 780. The BHA 626 telemetry signal data can be transmitted via telemetry system 606, with reference to FIG. 6. Referring again to FIG. 7, it should be understood that the term "interface" does not indicate a limitation to interfaces that use only Ethernet connections and refers to all possible external interfaces, wired or wireless. It should also be understood that the database 777, the; support computer or processor 775; and/or the pressure measurement data, the BHA telemetry signal data, the other telemetry signal data, the other databases, and/or the other processors 779 are not limited to interfacing with the one or more computers 555 using the network interface 780 and can interface with the one or more computers 555 in any means sufficient to create a communication path between the one or more computers 555 and the database 777; the support computer or processor 775; and/or the pressure measurement data, the BHA telemetry signal data, the other telemetry signal data, the other databases, and/or other processors 779. For example, in one or more embodiments, the database 777 can interface with the one or more computers 555 via a USB interface while the processor 775 can interface via some other high-speed data bus without using the network interface 780. The one or more computers 555, the processor 775, and the other processors 779 can be integrated into a multiprocessor distributed system.

It should be understood that even though the one or more computers 555 is shown as a platform on which the embodiments described can be performed, the embodiments described can be performed on any platform. For example, the many and varied embodiments described herein can be used on any device that has computing capability. For example, the computing capability can include the capability to access any communication bus protocols such that the user can interact with the many and varied computers 686, the databases 777; the support computers or processors 775; the pressure measurement data, the BHA telemetry signal data, the other telemetry signal data, the other databases, and/or the other processors 779 that can be distributed or otherwise assembled. These devices can include, but are not limited to and are presented for illustrative purposes only: supercomputers, arrayed server networks, arrayed memory networks, arrayed computer networks, distributed server networks, distributed memory networks, distributed computer networks, desktop personal computers (PCs), tablet PCs, hand held PCs, laptops, devices sold under the trademark names BLACKBERRY™ or PALM™, cellular phones, cellular smart phones, hand held music players, or any other device or system having computing capabilities.

Still referring to FIG. 7, programs can be stored in the one or more memories 720, and the one or more central processing units 710 can work in concert with at least the one or more memories 720, the one or more input devices 730, and the one or more output device s750 to perform tasks for the user. In one or more embodiments, the one or more memories 720 include any number and combination of memory devices, without limitation, as is currently available or can become available in the art. In one or more embodiments, memory devices can include without limitation, and for illustrative purposes only: the database 777; the support computer or processor 775; other databases, and/or other processors 779, hard drives, disk drives, random access memory, read only memory, electronically erasable programmable read only memory, flash memory, thumb drive memory, and any other memory device. Those skilled in the art are familiar with the many variations that can be employed using memory devices and no limitations should be imposed on the embodiments herein due to memory device configurations and/or algorithm prosecution techniques.

The one or more memories 720 can store an operating system (OS) 745, a stick slip analysis agent 725, and a drilling operations agent 732. The operating system 745 can facilitate control and execution of software using the one or more central processing units 710. Any available operating system can be used in this manner including WINDOWS™, LINUX™, Apple OS™, UNIX™, and the like.

The one or more central processing units 710 can execute either from a user request or automatically. In one or more embodiments, the one or more central processing units 710 can execute the drilling operations agent 732 when a user requests various drilling activities commence or terminate. The one or more central processing units 710 can execute the stick slip analysis agent 725 when a user requests, among other requests, to detect slick slip conditions during drilling activities. The stick slip analysis agent 725 can detect and communicate stick slip conditions to the drilling operations agent 732 and the drilling operations agent 732 can activate a controller to change drilling parameters, such as RPM, weight on a drill bit, etc., to alleviate the one or more stick slip conditions.

It should be noted that the stick slip analysis agent 725 and the drilling operations agent 732 can be fully autonomous code sets, partially integrated code sets, or fully integrated code sets, and no limitations should be construed from the depiction of the stick slip analysis agent 725 and the drilling operations agent 732 as separate agents. It should also be noted that it is not necessary to execute the stick slip analysis agent 725 and the drilling operations agent 732 simultaneously nor is it necessary to execute the two agents on the same one or more computers 555.

Referring again to FIG. 6, the data acquisition system 550 can be configured to host a plurality of software agents and/or models, such as a reservoir model, and to acquire and process data from downhole components and the at least one pressure measurement device 540, as well as determine the bottom hole location in the reservoir 615 from measurement while drilling data and/or from the length of the drill string. Examples of reservoir models and cross well interference testing can be found in the following references: "Interpreting an RFT-Measured Pulse Test with a Three-Dimensional Simulator" by Lasseter, T., Karakas, M., and Schweitzer, J., SPE 14878, March 1988; "Design, Implementation, and Interpretation of a Three-Dimensional Well Test in the Cormorant Field, North Sea" by Bunn, G. F., and Yaxley, L. M., SPE 15858, October 1986; "Layer Pulse Testing Using a Wireline Formation Tester" by Saeedi, J., and Standen, E., SPE 16803, September 1987; "Distributed Pressure Measurements Allow Early Quantification of Reservoir Dynamics in the Jene Field" by Bunn, G. F., Wittman, M. J., Morgan, W. D., and Curnutt, R. C., SPE 17682, March 1991; "A Field Example of Interference Testing Across a Partially Communicating Fault" by Yaxley, L. M., and Blaymires, J. M., SPE 19306, 1989; and "Interpretation of a Pulse Test in a Layered Reservoir" by Kaneda, R., Saeedi, J., and Ayestaran, L. C., SPE 19306, December 1991.

The drill rig 601 or a similar device can be used to move the drill string 605 through subterranean formations of the reservoir 615. The drill string 605 can be extended into the subterranean formations with a number of coupled drill pipes (one of which is designated 620) of the drill string 605. The drill pipe including the drill string 605 can be structurally similar to known drill pipe and can include a cable associated with each drill pipe 620 that can serve as a telemetry communication channel.

The BHA 626 at the lower end of the drill string 605 can include one, an assembly, or a string of downhole tools. In the illustrated example, the drill string 605 can include well logging tools 625 coupled to a lower end thereof. As used in the present description, the term well logging tool or a string of such tools can include at least one or more logging while drilling tools, formation evaluation tools, formation sampling tools, and other tools capable of measuring a characteristic of the subterranean formations of the reservoir 615 and/or of the borehole 665.

Several of the components disposed proximate to the drill rig 601 can be used to operate components of the overall system. These components will be explained with respect to their uses in drilling the borehole 665. The drill string 605 can be used to turn and/or urge a drill head or drill bit 616 into the borehole 665 to increase the drill string 605 length and/or depth. Drill motors (not shown) within the drill bit 616 can be used to urge the drill bit 616 into the borehole 665. The motors can be electric motors and can be electrically powered by components such as batteries, electrical generation turbines, and/or other known electrical storage and/or electrical generation components.

During drilling, one or more pumps 630 can lift drilling fluid or drilling mud from one or more tanks, troughs, or pits 640 and can discharge the drilling fluid 635 under pressure through a standpipe 645 and flexible conduit 650, through a top drive 655 and into an interior passage inside the drill pipe 620. The drilling fluid 635, which can be water or oil-based, can exit the drill pipe 620 through courses or nozzles (not shown) in the drill bit 616, wherein it can cool and/or lubricate the drill bit 616 and can lift drill cuttings generated by the drill bit 616 to the surface through an annular or other known arrangement and recycled back into the one or more tanks, troughs, or pits 640.

When the borehole 665 has been drilled to a selected depth, the well logging tools 625 can be positioned at the lower end of the borehole 665 if not previously disposed within or on the drill string 605. The well logging tools 625 can be positioned by pumping the well logging tools 625 down the drill string 605 or otherwise moving the well logging tools 625 down the drill string 605 while the drill string 605 is within the borehole 665. The well logging tools 625 can then be coupled to an adapter sub 660 within the vicinity of the end of the drill string 605 and can be moved through, for example as illustrated, an inclined portion of the borehole 665.

During well logging operations, the pumps 630 can be operated to provide fluid flow to operate one or more turbines in the well logging tools 625 to provide power to operate certain devices in the well logging tools 625. When tripping in or out of the borehole 665, (turning on and off the pumps 630) it can be unfeasible to provide fluid flow. As a result, power can be provided to the well logging tools 625 in other ways. For example, batteries can be used to provide power to the well logging tools 625. In one embodiment, the batteries can be rechargeable batteries and can be recharged by turbines during fluid flow. The batteries can be positioned within the housing of one or more of the well logging tools 625. Other configurations and methods of powering the well logging tools 625 can be used including, but not limited to, one-time power use batteries.

As the well logging tools 625 are moved along the borehole 665 by moving the drill pipe 620, signals can be detected by various devices, of which non-limiting examples can include a resistivity measurement device, a bulk density measurement device, a porosity measurement device, a formation capture cross-section measurement device 670, a gamma ray measurement device 675 and/or a formation fluid sampling tool 668 which can include a formation at least one pressure measurement device. The signals can be transmitted toward the surface of the earth along the drill string 605.

An apparatus and/or system for communicating from the drill pipe 620 to the data acquisition system 550 or other component configured to receive, analyze, and/or transmit data can include a second adapter sub 690 that can be coupled between an end of the drill string 605 and the top drive 655 that can be used to provide a communication channel with a receiving unit 695 for signals received from the well logging downhole tools 625, the at least one pressure measurement device 540, the telemetry system 606, and/or other telemetry transmitting devices, not shown. The receiving unit 695 can be coupled to the data acquisition system 550 to provide a data path therebetween that can be a bidirectional data path. Although the receiving unit 695 and the data acquisition system 550 are depicted as separate components, they can be fully or partially integrated, and no limitations should be assumed based on the illustrated embodiment.

Though not shown, the drill string 605 can be connected to a rotary table, via a Kelly, and can suspend from a traveling block or hook 603, and additionally a rotary swivel. The rotary swivel can be suspended from the drill rig 601 through the hook 603, and the Kelly can be connected to the rotary swivel such that the Kelly can rotate with respect to the rotary swivel. The Kelly can be any configuration. For example, the Kelly can include a set of polygonal connections or splines on the outer surface that mate to a Kelly bushing such that actuation of the rotary table can rotate the Kelly. An upper end of the drill string 605 can be connected to the Kelly, such as by threadingly reconnecting the drill string 605 to the Kelly, and the rotary table can rotate the Kelly, thereby rotating the drill string 605 connected thereto.

Although not shown, the drill string 605 can include one or more stabilizing collars. A stabilizing collar can be disposed within or connected to the drill string 605, in which the stabilizing collar can be used to engage and apply a force against the wall of the borehole 665. This can enable the stabilizing collar to prevent the drill pipe 620 from deviating from the desired direction for the borehole 665. For example, during drilling, the drill string 605 can "wobble" within the borehole 665, thereby allowing the drill string 605 to deviate from the desired direction of the borehole 665. This wobble action can also be detrimental to the drill string 605, components disposed therein, and the drill bit 616 connected thereto. A stabilizing collar can be used to minimize, if not overcome altogether, the wobble action of the drill string 605, thereby possibly increasing the efficiency of the drilling performed at the well site 600 and/or increasing the overall life of the components at the well site 600.

Example embodiments can include the drill string 605 within the borehole 665. The at least one pressure measurement device 540 can be disposed in fluid communication with the drilling fluid 635. The at least one pressure measurement device 540 can include, but is not limited to, one or more pressure transducers, one or more accelerometers, and/or one or more gyroscopic devices. The at least one pressure measurement device 540, for example a pressure transducer, can be placed in fluid communication with the drilling fluid to detect or measure pressure waves within the drilling fluid 635 and generate pressure measurement data. The contact between the at least one pressure measurement device 540 and the drilling fluid 635 can be at the surface or anywhere within the borehole 665.

During drilling operations, the pressure measurement data can be used to provide real time data on the phase and strength of oscillations, including those indicating the one or more stick slip conditions, within the pressure measurement data. During drilling operations, the stick slip analysis agent 725 can be used to analyze the pressure measurement data to detect the one or more stick slip conditions.

An analysis can be performed on the pressure measurement data as it is received to detect the one or more stick slip conditions from the one or more variations in the pressure measurement data. Numerical analysis can be performed on the pressure measurement data to determine if the detected variations in the pressure measurement data are the result of drilling activity, such as mud pump operations, and distinguished from the stick slip oscillations.

The detected stick slip conditions information can be fed to the drilling operations agent 732. The drilling operations agent 732 can change the drilling mechanics, such as torque, weight on the drill bit, revolutions per minute (RPM) etc. so as to damp out the one or more stick slip conditions. In an embodiment, a feedback algorithm can be developed to change the rate at which the drill rig 601 extends its pads so as to reduce the one or more stick slip conditions. The pressure measurement data can be used within the one or more computers 555 in combination with one or more damping algorithm agents known in the art, not shown, to control the damping. By including the pressure measurement data during the one or more stick slip conditions, drill string torque, among other factors, can be accounted for within the damping algorithm agents.

The pressure measurement data indicating stick slip conditions can be processed in the data acquisition system 550 and compared to at least one preset threshold. The at least one preset threshold can be selected based on the particular construction of the drill string and/or the drill string's known, estimated, and/or calculable resonance frequencies. If at least one preset threshold is met and/or exceeded, in other words the one or more variations in the pressure measurement data exceed an acceptable limit, the drilling operations agent 732 can be commanded to change drilling parameters, such as RPM, weight on the drill bit, etc., to alleviate the one or more stick slip conditions. For example, the top drive 655 can be autonomously slowed or a weight on the drill bit 616 can be reduced.

It has been discovered that one or more torque measurements indicating the torque on the drill bit 616 can be taken from the drill string 605 and can indicate stick slip conditions using techniques similar to those described above. The one or more torque measurements can be correlated to the one or more stick slip conditions by searching for variations in the one or more torque measurements consistent with the one or more stick slip conditions. The one or more torque measurements can be converted into torque measurement data. Spectral analysis can be performed on the torque measurement data, and an analysis of the frequency spectrum of the torque measurement data can be performed to identify the one or more stick slip conditions from the variations in the torque measurement data. The torque measurement data indicating the one or more stick slip conditions can be compared to the pressure measurement data that indicates the one or more stick slip conditions or vice versa. The comparison can be used as a verification that the one or more stick slip conditions exist. The torque measurement data can be used as an independent indicator of the existence of the one or more stick slip conditions. The torque measurement data can be used to complement the pressure measurement data that indicates the one or more stick slip conditions. The pressure measurement data can be used as an independent indicator of the existence of the one or more stick slip conditions and/or to verify and/or to complement the torque measurement data indicating the one or more stick slip conditions.

During drilling operations, one or more torque measurements can be taken from drill string 605 and can be used to indicate the existence of one or more stick slip conditions. The one or more torque measurements can be taken directly from the drill string 605, the top drive 655, the Kelly, the second adapter sub 690, the drill bit 616, and/or from any component attached to the drill string 605 and transmitted to the data acquisition system 550. The one or more torque measurements can be calculated from a measurement of the amount of power sent to the drill bit 616 motors, not shown, as a function of the amount of power sent to the drill bit 616 motors during drilling operations, or can be calculated or measured using any known method. For example, the one or more computers 555 can calculate the one or more torque measurements from a measurement of the amount of power sent to the drill bit 616 motors during drilling operations using known methods.

Torque can propagate along the drill string 605. The communication channel for torque can be within and along the drill pipe 620. The propagation of the torque can be governed by the speed of sound in steel and each segment of the drill pipe 620 can act as a reflector of the torque. The propagation of the one or more pressure waves within the drilling fluid 635 can be governed by the speed of sound of the drilling fluid 635 or any fluid in fluid communication with the drill bit 616. The propagation of both the torque on the drill bit 616 and the one or more pressure waves within the drilling fluid 635 can be subject to multipath affects.

It has been discovered that if the at least one pressure measurement device 540 is disposed on, within, or near the BHA 626 and the one or more stick slip conditions are detected by a data acquisition system 550 disposed on, within, or near at the BHA 626 based on the pressure measurement data from the at least one pressure measurement device 540, the length of the drill string can be calculated by the data acquisition system 550 and the length can be correlated to the depth of the BHA 626. Embodiments can include automatic BHA 626 operations based on the depth of the BHA 626 where at least one operational parameter of the BHA 626 can be changed based on the depth of the BHA 626. For example, when the BHA 626 reaches a certain depth, a BHA 626 controller can change the direction of the BHA 626, switch between one or more sensors, and/or activate and/or deactivate any device within the BHA 626, and/or change any other operational parameter of the BHA 626. Recording the depth of the BHA 626 in a memory of the BHA 626 can be utilized to compensate for the differences between a surface clock and a clock disposed on, within, and/or near the BHA 626.

During the one or more stick slip conditions, a device (not shown) can be disposed in the BHA 626, or somewhere else in the drill string 605, or on the surface of the BHA 626 or drill string 605 and the device can create an equal and opposite pressure wave. Such pressure wave can be used to effectively dampen the one or more stick slip conditions. The arrangement can include a motor actuated valve, not shown, that can fluctuate pressure within the drilling fluid to counteract the pressure received by the one or more stick slip conditions. In an embodiment, a mud motor can be used to reduce the effects of the one or more stick slip conditions.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

Although only a few example embodiments have been described in detail above, those skilled in the art will readily appreciate that many modifications are possible in the example embodiments without materially departing from "Determination of Stick Slip Conditions." Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw can not be structural equivalents in that a nail employs a cylindrical surface to secure wooden parts together, whereas a screw employs a helical surface, in the environment of fastening wooden parts, a nail and a screw can be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method for determining stick slip conditions, comprising:
    disposing an operating apparatus in fluid communication with a pressure wave transmission medium;
    disposing at least one pressure measurement device at least partially within the pressure wave transmission medium and at some distance from the operating apparatus;
    measuring one or more pressure waves generated by the operating apparatus within the pressure wave transmission medium with the at least one pressure measurement device and generating pressure measurement data therefrom;
    transmitting the pressure measurement data from the at least one pressure measurement device to a data acquisition system; and
    analyzing the pressure measurement data using the data acquisition system to detect one or more stick slip conditions from one or more variations in the pressure measurement data.

2. The method of claim 1, comprising:
    determining at least one resonance frequency of the apparatus;
    analyzing telemetry signal data from the apparatus within the at least one resonance frequency to detect the one or more stick slip conditions from one or more variations in the telemetry signal data; and comparing the one or more variations in the telemetry signal data to the one or more variations in the pressure measurement data.

3. The method of claim 1, wherein the pressure measurement data is analyzed using spectral analysis.

4. The method of claim 1, comprising:
comparing the one or more variations in the pressure measurement data to at least one preset threshold; and
changing at least one operational parameter of the apparatus such that the one or more stick slip conditions is moderated if the at least one preset threshold is exceeded by the one or more variations in the pressure measurement data.

5. The method of claim 1, further comprising:
determining a resonance frequency of the operating apparatus; and
analyzing the pressure measurement data within a frequency band that includes the resonance frequency to detect the one or more stick slip conditions from the one or more variations in the pressure measurement data.

6. The method of claim 1, further comprising analyzing telemetry signal data from the apparatus, and wherein analyzing the pressure measurement data comprises comparing one or more variations in the telemetry signal data to the one or more variations in the pressure measurement data.

7. A method for determining stick slip conditions on a drill string in a borehole, comprising:
disposing at least one pressure measurement device in fluid communication with a drilling fluid disposed within a borehole;
disposing a bottom hole assembly coupled to a drill string within the borehole and in fluid communication with the drilling fluid;
measuring pressure waves within the drilling fluid and generating pressure measurement data therefrom;
transmitting the pressure measurement data to a data acquisition system;
detecting a stick slip condition from one or more variations in the pressure measurement data using the data acquisition system;
comparing the one or more variations in the pressure measurement data to a threshold; and
controlling a progression of the drill string within the borehole if the one or more variations in the pressure measurement data exceed the threshold.

8. The method of claim 7, comprising:
distinguishing the pressure measurement data associated with the operations of the drill string from the one or more variations in the pressure measurement data that indicate the one or more stick slip conditions.

9. The method of claim 7, wherein controlling the progression of the drill string comprises adjusting a weight on a drill bit of the drill string.

10. The method of claim 7, comprising disposing the at least one pressure measurement device at a surface location of a well site having the drill string disposed within the borehole.

11. The method of claim 7, comprising:
determining a torque on a drill bit connected to the bottom hole assembly;
converting the torque into torque measurement data;
transmitting the torque measurement data to the data acquisition system;
detecting one or more stick slip conditions from one or more variations in the torque measurement data; and
comparing the one or more variations in the torque measurement data to the one or more variations in the pressure measurement data to confirm that at least one stick slip condition exists.

12. The method of claim 7, wherein spectral analysis is utilized for detecting variations in the pressure measurement data.

13. The method of claim 12, wherein Welch's methods are utilized for detecting variations in the pressure measurement data.

14. The method of claim 7, comprising:
calculating the depth of the bottom hole assembly within the borehole based on a frequency of the one or more variations in the pressure measurement data that indicates a stick slip condition; and
changing at least one operational parameter of the bottom hole assembly based on the depth of the bottom hole assembly within the borehole.

15. The method of claim 7, comprising:
calculating the depth of the bottom hole assembly within the borehole based on a frequency of the one or more variations in the pressure measurement data that indicates a stick slip condition; and
recording the depth of the bottom hole assembly within a memory of the bottom hole assembly.

16. The method of claim 7, wherein the method further comprises:
analyzing telemetry signal data from the drill string for one or more noise signals;
determining one or more noise frequency bands from the one or more noise signals;
searching within at least one noise frequency band to detect the one or more stick slip conditions from one or more variations in the telemetry signal data; and
comparing the one or more variations in the telemetry signal data to the one or more variations in the pressure measurement data.

17. A system for detecting stick slip conditions, comprising:
a drill string disposed in a borehole at a well site;
a first pressure measurement device disposed at some distance from the drill string, wherein the first pressure measurement device is in fluid communication with a drilling fluid disposed within the borehole, and wherein the first pressure measurement device is adapted to measure one or more pressure waves within the drilling fluid; and
a first data acquisition system disposed at a surface location of the well site, wherein the first data acquisition system is adapted to receive and process pressure measurement data from the first pressure measurement device, and wherein the first data acquisition system is adapted to detect one or more stick slip conditions from one or more variations in the pressure measurement data and adapted to compare the variations in the pressure measurement data to a threshold.

18. The system of claim 17, wherein the pressure measurement device is disposed at a surface location of the well site, and the threshold is a preset threshold.

19. The system of claim 17, further comprising a controller adapted to control a progression of the drill string within the borehole based upon the variations exceeding the threshold.

20. The system of claim 19, wherein the controller is adapted to decrease a rotational speed of the drill string.

21. The system of claim 19, wherein the controller is adapted to adjust a weight on a drill bit of the drill string.

22. The system of claim 17, further comprising:
a bottom hole assembly coupled to the drill string;
a second pressure measurement device coupled to the bottom hole assembly;
a second data acquisition system disposed within the bottom hole assembly adapted for calculating the depth of the bottom hole assembly within the borehole based on the frequency of the one or more variations in the pressure measurement data caused by the one or more stick slip conditions; and
a bottom hole assembly controller adapted for changing at least one operational parameter of the bottom hole assembly based on the calculated depth of the bottom hole assembly within the borehole.

* * * * *